United States Patent
Lembeye

(10) Patent No.: US 6,388,439 B1
(45) Date of Patent: May 14, 2002

(54) METHOD AND DEVICE FOR MEASURING IN SITU THE GAP BETWEEN TWO GIVEN ELEMENTS IN A TUBULAR PIPE

(75) Inventor: Philippe Lembeye, Caudebec-En-Caux (FR)

(73) Assignee: Coflexip (FR)

( * ) Notice: Subject to any disclaimer, the term of this patent is extended or adjusted under 35 U.S.C. 154(b) by 0 days.

(21) Appl. No.: 09/443,167

(22) Filed: Nov. 19, 1999

(30) Foreign Application Priority Data

Feb. 19, 1999 (FR) .......................................... 99 02089

(51) Int. Cl.$^7$ ............................. G01N 27/72; G01B 7/14
(52) U.S. Cl. .................... 324/220; 324/207.16; 702/77; 33/544.5; 33/544
(58) Field of Search ...................... 33/542, 543, 544, 33/544.2, 544.5, 613; 324/220, 221; 702/77, 190, 191, 193, 194, 195, 196, 197; 708/300, 303, 309, 311, 819–829, 503–505; 304/207.16

(56) References Cited

U.S. PATENT DOCUMENTS

| | | | | |
|---|---|---|---|---|
| 3,238,448 A | * | 3/1966 | Wood et al. | ................... 324/37 |
| 3,460,028 A | * | 8/1969 | Beaver et al. | ............ 324/34 R |
| 3,732,625 A | * | 5/1973 | Vernooy | ................... 33/141 |
| 3,786,684 A | * | 1/1974 | Wiers et al. | ................... 73/432 |
| 3,967,194 A | | 6/1976 | Beaver | ................... 324/37 |
| 4,835,876 A | * | 6/1989 | Petermann et al. | ............ 33/313 |
| 4,858,144 A | * | 8/1989 | Marsaly et al. | ............. 364/496 |
| 4,964,059 A | * | 10/1990 | Sugaya et al. | ............... 364/507 |
| 5,068,608 A | | 11/1991 | Clark, Jr. | ................... 324/220 |
| 5,532,587 A | | 7/1996 | Downs | ................... 324/220 |
| 5,574,223 A | * | 11/1996 | Kiefer | ................... 73/623 |
| 5,640,780 A | * | 6/1997 | Kermabon | ................... 33/544 |
| 5,645,109 A | * | 7/1997 | Herrero et al. | ............. 138/134 |
| 6,243,657 B1 | * | 6/2000 | Truck et al. | ................ 702/150 |
| 6,204,659 B1 | * | 3/2001 | Yamamoto | ............. 324/207.16 |

FOREIGN PATENT DOCUMENTS

| | | |
|---|---|---|
| EP | 0304053 | 2/1989 |
| FR | 9508635 | 9/1997 |
| GB | 2102565 | 2/1983 |
| GB | 2301414 | 12/1996 |
| JP | 355060805-00 | * 10/1978 ................. 324/220 |

OTHER PUBLICATIONS

E.C. Young, Dictionary of Electronics, Laurence Urdang Associates Ltd, 1979, p. 221.*

* cited by examiner

*Primary Examiner*—Diego Gutierrez
(74) *Attorney, Agent, or Firm*—Ostrolenk, Faber, Gerb & Soffen, LLP

(57) ABSTRACT

Method for measuring the gap separating a vault of at least one end fitting and a given element of one end of a thermal part of a pipe, comprising; moving an autonomous measuring detector inside the said pipe, carrying out at least one series of measurements during the movement of the detector in the end fitting, the measuring comprising detecting in real time, the passage of the consecutive transitions between the vault of the end of the terminal part of the pipe, triggering the measurements for a predetermined time between the detections of the transitions, storing the said measurements in the form of signals in at least one memory and processing the stored signals in order to determine the gap (D) and separating two consecutive transitions. The device for measuring includes two eddy current detectors on a support wound through the pipe and a memory for the detected signals and a processing circuit for processing the signals in memory.

3 Claims, 4 Drawing Sheets

METHOD AND DEVICE FOR MEASURING IN SITU THE GAP BETWEEN TWO GIVEN ELEMENTS IN A TUBULAR PIPE

BACKGROUND OF THE INVENTION

The present invention relates to a method and a device for measuring in situ the gap separating two given elements in a tubular pipe.

A flexible pipe usually includes an end fitting at each end. The end fittings are members which allow the flexible pipes to be connected to stationary structures such as a structure floating on the surface of the sea and anchored to the seabed or else a structure placed on the seabed such as, for example, a well head or a manifold. End fittings may also be used for joining lengths of flexible pipe when the latter has a long length. The greater the length of the pipe (several kilometers), the larger the number of mid-connectors used.

The pipes targeted by the present invention are those which are called "rough bore", which comprise a carcass as the innermost element and placed over this carcass is an inner sheath, of the type described in the American Petroleum Institute 17J and American Petroleum Institute 17B standards.

In general, one end of the pipe is mounted and fastened inside the end fitting by suitable means which are well known and will not therefore be described.

An end fitting has two functions, one external and the other internal. The external function consists in connecting the end fitting to a structure regarded as being stationary, using a connection flange for example. The internal function is provided by a vault and clamping means which allow the sealing continuity of the flexible pipe to be maintained, the inner sheath being clamped onto the carcass by means of, for example, a monocone. The end of a pipe is mounted and fastened in the end fitting in such a way that a stop ring, welded to the end of the carcass, is located at a certain distance from the vault of the end fitting.

However, during any period of use of the pipe, it is necessary to measure the gap separating the stop ring from the vault of the end fitting. In fact, even a very slight displacement of the stop ring, integral with the carcass, with respect to the vault of the end fitting may mean a relative displacement of the inner sheath with respect to the pressure vault. Such a displacement of the inner sheath may cause a loss of sealing, which would be prejudicial to proper operation of the pipe. It would then be essential to change the pipe. The relative displacement of the inner sheath with respect to the pressure vault may arise from a reduction in the clamping force exerted by the monocone on the inner sheath. Modification of the properties of the inner sheath may also cause a displacement of the sheath, the modification possibly being a result of temperature fluctuations of the fluid flowing in the pipe.

In non-destructive testing of a pipe, such as the testing described for example in Patent FR-B-95/08635, it is possible to use an eddy-current sensor to detect defects in the product to be tested. Eddy-current testing consists in mounting a sensor on a pig which is moved in the pipe using suitable means, such as a pressurized fluid. The sensor produces eddy currents in the pipe which generate in turn a variable reactive magnetic field. The field affects the impedance of a receiving coil placed near the surface to be tested. In the presence of a defect, the circulation of eddy currents is disturbed by the defect, thereby causing variations in the reactive field and therefore in the impedance of the receiving coil. Measuring the impedance should make it possible to detect the presence of defects in the product. The precise position of the defects is not known but can be determined to within about one meter. However, the amplitude of the signal coming from the receiving coil depends on the dimensions of the defect, mainly the depth and the width of the defect. The amplitude of the signal also depends on the electromagnetic properties of the walls of the defect.

However, the eddy-current sensor as normally used cannot allow the size of the defect to be easily determined. This size can be measured only if the speed of movement of the sensor, on passing over the defect, is known very precisely, and only if the speed is constant. One solution recommended by specialists consists in bringing in and immobilizing a scanner right at the defect to be measured and in scanning the defect at a predetermined and constant speed. Such a solution is difficult to employ in the case of a long pipe having a large number of defects to be measured, since it in particular requires the defects to be accurately located along the pipe in order to bring the scanner in line with the defect. The scanning may be carried out by eddy currents, ultrasound or other means.

However, scanning is limited to lengths of flexible pipe not exceeding 5000 m because of the capstan effect which is liable to occur in the curved parts of the flexible pipe. The capstan effect possibly in turn induces an elongation of the umbilical at the end of which the sensor is mounted.

In order to avoid the capstan effects, it is conceivable to use autonomous pigs carrying the sensors and the data acquisition and storage means. The sensors mounted on these autonomous pigs may either be of the leakage-flux type. But then there is a difficult problem to be solved when the strip and/or the ring is made of non-magnetic material. The sensors may be of the ultrasound type, and then any impurities located in the defect may falsify the measurement appreciably since the defect may be hidden by these impurities, and the defect is then no longer detected.

A coding wheel cannot be envisaged for bringing the scanner onto the defect since not only can it slide on the carcass but it is also disturbed by the irregular shape of the internal wall of the carcass.

Another solution would consist in calibrating the current sensor according to a given type of defect. To do this, the sensor would have to be calibrated using several pipes which serve only for the calibration and which must have very precisely the defect desired, both in its size and its structure and the constituent materials of the flexible pipe and of the end fitting in which it is desired to detect a defect. These calibration pipes are new every time a pipe to be tested is changed. This entails a considerable cost and a very lengthy measurement time, including the calibration time. In reality, such a solution cannot be envisaged on an industrial scale.

It is also possible to use a so-called low-resolution sensor and to carry out a correlation between, on the one hand, the shape and amplitude of the signal and, on the other hand, the size of the defect. But this requires tedious and stringent calibration techniques.

The amplitude of the processed signal increases with the width of the defect detected.

Another technique consists in using a so-called high-resolution sensor which allows the edges of the defect to be detected sequentially. In this case, the amplitude of the processed signal remains constant whatever the width of the defect, but this would not avoid a calibration as indicated above.

SUMMARY OF THE INVENTION

The object of the present invention is to remedy the aforementioned drawbacks of the known solutions and to propose a method and a device for accurately measuring the gap separating the vault of the end fitting from the stop ring or carcass, which are not sensitive to the speed of movement and/or variations in the speed of movement of the pig, which does not require knowing in advance the position of the gap or gaps when the pipe comprises several end fittings along its entire length, which are compatible with the measurement environment and which minimize the complexity of the electronics for data processing and storage.

It has been found that, contrary to what was accepted by the experts, the eddy currents could be used simply by combining at least two sensors mounted in tandem and separated by a fixed interval, as will be described below.

The subject of the present invention is a method for measuring the gap separating a vault of an end fitting from the end of an inner carcass of a pipe, of the comprising in:
  moving autonomous measurement means inside the pipe at a speed which may vary,
  carrying out at least one series of measurements during the movement of the measurement means in the end fitting,
  storing the measurements in the form of signals in at least one memory,
  processing the said signals,
and it further comprises
  detecting, in real time, the passage of the consecutive transitions between the vault of the end fitting and the end of the terminal part of the pipe,
  triggering the measurements for a predetermined time between the detections of the said transitions and
  processing the stored signals in order to determine the gap separating two consecutive transitions.

Another subject of the present invention is a device for implementing the above method. The device comprising a support which is propelled inside the pipe by means such as a pressurized fluid, at least one high-resolution eddy-current sensor mounted on the support, means for storing the signals delivered by the sensor, at least two eddy-current sensors which detect in real time the transitions located on either side of a gap delimited between the vault of the end fitting and the stop ring of the carcass, and the said sensors are located a short distance from the internal wall of the pipe.

BRIEF DESCRIPTION OF THE DRAWINGS

Other advantages and characteristics will become more apparent on reading the description of several embodiments of the device for implementing the method according to the invention, as well as from the appended drawings in which.

DESCRIPTION OF A PREFERRED EMBODIMENT

Figure 1:
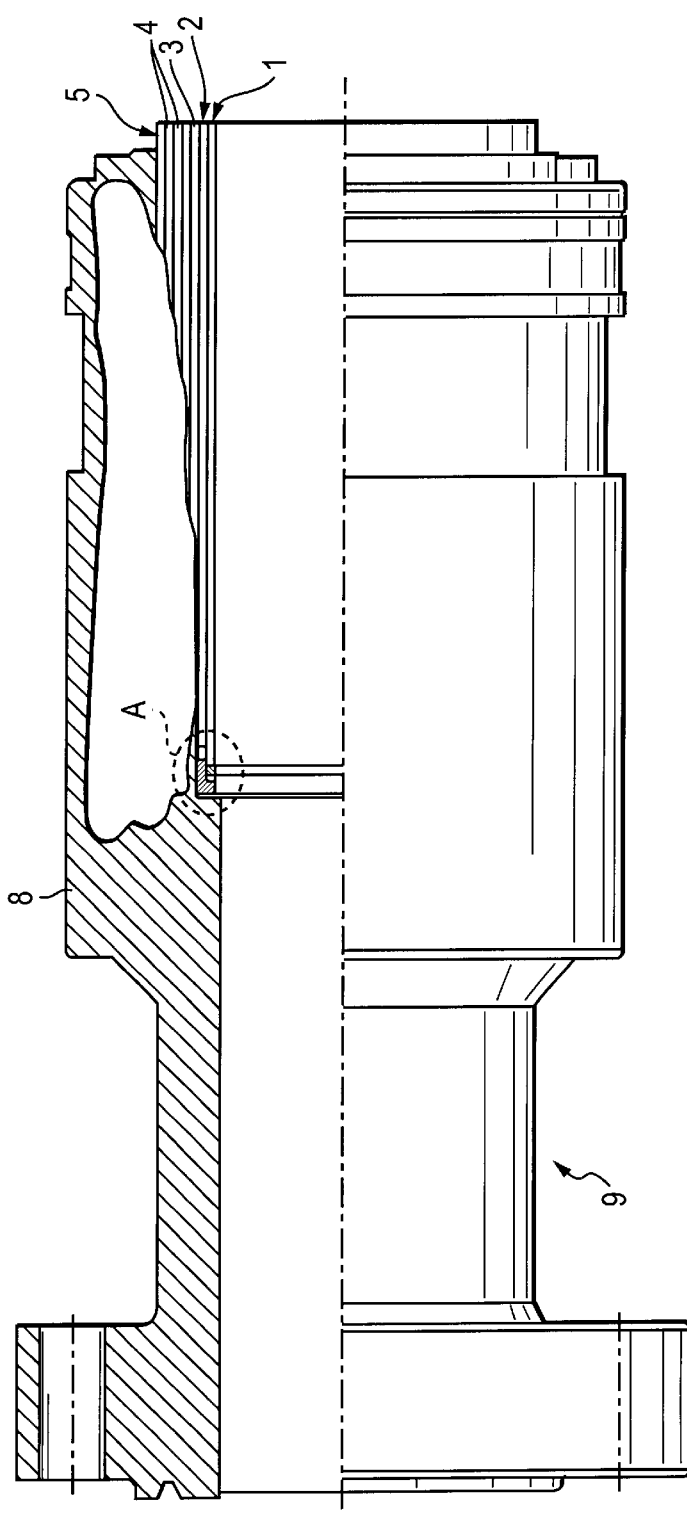
FIG. 1 is a view, in partial cross section, of an end fitting and one end of a pipe.

The flexible pipes relevant to the present invention are of the "rough bore" type, which can be used in the oil industry and which comprise, from the inside outwards:

an inner carcass 1 formed from an interlocked, profiled metal strip spiralled with a short pitch, which withstands the compressive loads on the pipe;

an inner sheath 2 which is generally extruded over the said carcass 1 and which is supported by the latter;

a pressure vault 3 consisting of at least one metal wire, for example made of ferromagnetic carbon steel, spiralled with a short pitch, and which has the function of withstanding the circumferential component of the internal pressure loads exerted by the fluid flowing in the pipe;

one or more armor plies 4 which consist of steel wires spiralled with a long pitch and surrounding the pressure vault 3 and which are intended mainly to withstand the axial tensile loads generated by the internal pressure of the fluid, the deadweight of the pipe, etc. These armor wires may have various cross-sectional shapes, for example rounded or rectangular cross section. The wires are then arranged beside each other in order to form a ply, or else they have cross sections of the interlockable type, such as a zeta cross section, a V-shaped cross section, a T-shaped cross section, an I-shaped cross section, etc.; and an outer sheath 5 made of a thermoplastic.

The carcass 1, has a thickness which may vary from a few millimeters to 15 mm or more, and is usually formed by a strip made of electrically conducting austenitic stainless steel, such as the grades 316/316L or 304/304L, or other grades of steel. The carcass 1 may therefore be non-magnetic, slightly magnetic or magnetic.

One end of a pipe or of part of a pipe, when these pipes consist of several lengths of pipe joined together, is located inside a vault of an end fitting. The positioning and fastening of the pipe end in the vault of the end fitting are well known to experts and will therefore not be described in more detail.

Figure 2:
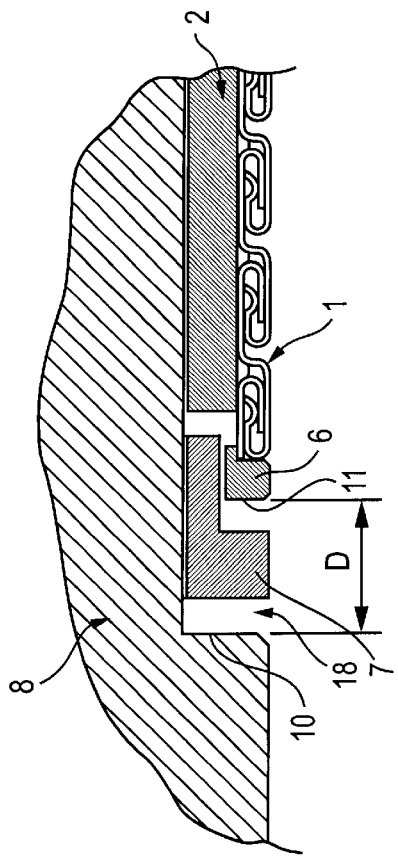
FIG. 2 is an enlarged view of detail A in FIG. 1.

The carcass 1, as shown in FIG. 2, is terminated by a stainless steel stop ring 6, the stop ring 6 is welded to the carcass 1. An electrical isolation ring 7, in the form of a lying-down L, is interposed between the stop ring 6 and the vault 8 of an end fitting 9. The vault 8 is made from a steel which is coated with nickel or with Inconel and which is conducting and magnetic or non-magnetic.

The device according to the invention is intended to measure the gap D separating the shoulder 10 of the end-fitting vault 8 from the spaced away surface 11 of the stop ring 6. Which are separated by the isolation ring 7

The method according to the invention comprises in:
  moving a pig in the pipe, the pig being of known type and comprising a specific module at the front;
  using a first sensor of the specific module detecting the transitions between the stop ring 6 and the end-fitting vault 8;
  detecting the same transitions as above by means of a second sensor provided in the specific module, the sensors being separated by a fixed and constant interval;
  storing the signals delivered by each of the sensors in a memory; and then
  processing the stored signals in order to determine the gap D between the transitions, the latter being delimited by the shoulder 10 and the surface 11 in the example illustrated.

Figure 3:
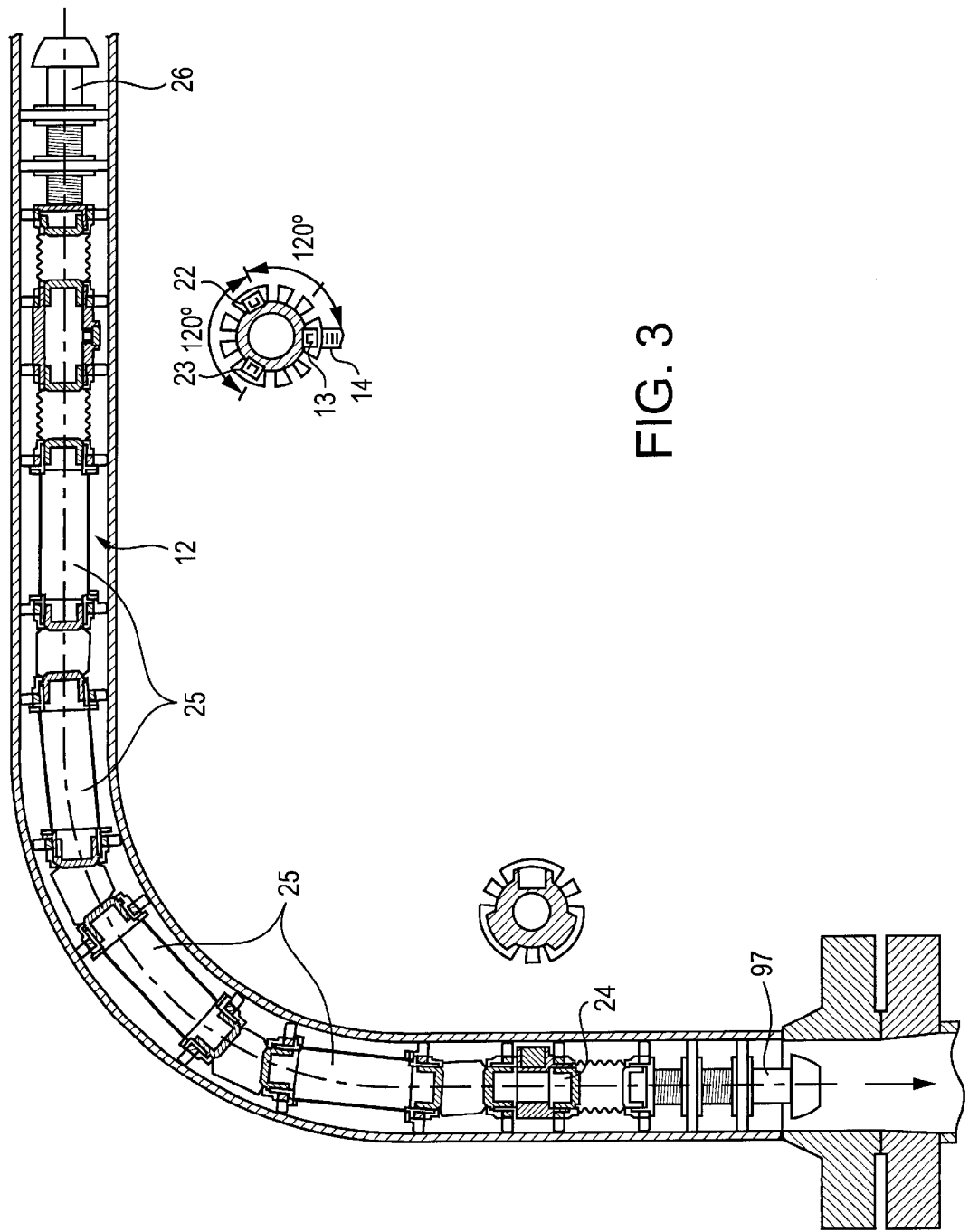
FIG. 3 is a partial cross-sectional view of the pipe in which a pig is housed.
Figure 4:
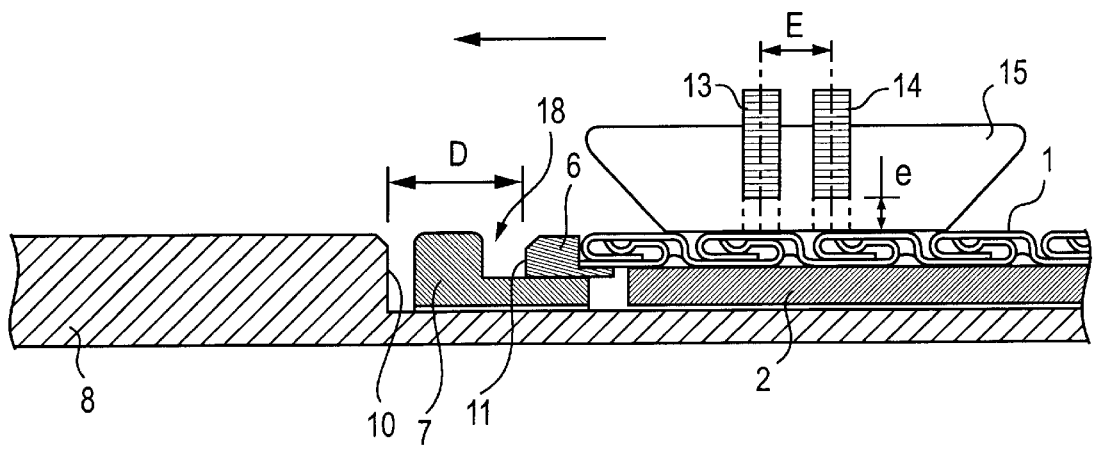
FIG. 4 is a partial schematic view of a specific module moving in the pipe.

A first embodiment of a device for implementing the method is illustrated in FIGS. 3 and 4. In this example, the determination of gap D is carried out from the shoulder 10 to the surface 11. However the determination between the surface 11 and the shoulder 10 may be carried out depending on the first transition detected by the first sensor.

In this embodiment, a support consists of a pig 12 on which a first sensor 13 and a second sensor 14 are mounted. The sensors are separated by a fixed and constant interval E. The two sensors are of the same type, for example eddy-current sensors, possibly mounted on a support or ski 15 incorporated into a specific module. The two sensors 13 and 14 are spaced at a certain radial distance from the vault 8 or from the stop ring 6 so that the air gap e left between the sensors and the vault 8 is between 3 and 15 mm. Each sensor 13, 14 works in absolute mode at a high frequency of between 10 kHz and 3 MHz, so as to optimize the signal/noise ratio and thus minimize the effects of the variations in electromagnetic properties, so that the amplitude of the signal delivered by the sensors is independent of the speed of passage of the pig within the drive-speed range lying between 0.1 and 3 m/s. Each sensor 13, 14 is linked to electronic means standard in the eddy-current technique, which electronic means provide the X and Y components of the signal delivered by each sensor in an impedance plane. The X and Y signals of each sensor 13, 14 are then sampled, digitized and stored for the purpose of subsequently processing the data at the end of measurement or of inspection.

For a gap D of approximately 50 mm and for a low speed of movement of the ski 15, for example about 0.2 m/s, but the acceleration of which is assumed to be constant during the measurements between the transitions 10 and 11, each sensor is excited for a relatively long period of time so as to be sure that the entire gap D is covered by the measurements. Preferably, the sensors are continuously excited, whereas the storage of the signals delivered by the sensors is limited over time, for example limited to one second, so as to avoid saturating the memories.

The first sensor 13 successively detects the transitions 10 and 11, the signals being generated continuously.

When the first sensor 13 lies opposite the carcass 1, the signals delivered by the said sensor, and for a given position, encounter the various layers of the interlocked turns of the carcass 1, the inner sheath 2 and the vault 8 of the end fitting. The complex impedance of the signals is portrayed by the cloud 16 in FIG. 5 which shows the impedance in a complex (real and imaginary) plane. When the sensor 13 lies opposite the stop ring 6, the corresponding impedance of the signals delivered by the sensor 13 is portrayed by the spot or area 17 in FIG. 5. When the same sensor 13 reaches the interval 18 (of gap D) between the stop ring 6 and the shoulder 10 of the end-fitting vault 8, the impedance of the signals delivered by the sensor 13 varies suddenly and is portrayed by the spot or area 19 in FIG. 5. The isolation ring 7 has no influence on the impedance because of the material used. While the sensor crosses the interval 18, the impedance of the signals virtually does not vary until the sensor reaches the transition consisting of the shoulder 10 of the vault 8. This impedance on the vault 8 is portrayed by the cloud of spots 20.

Figure 5:
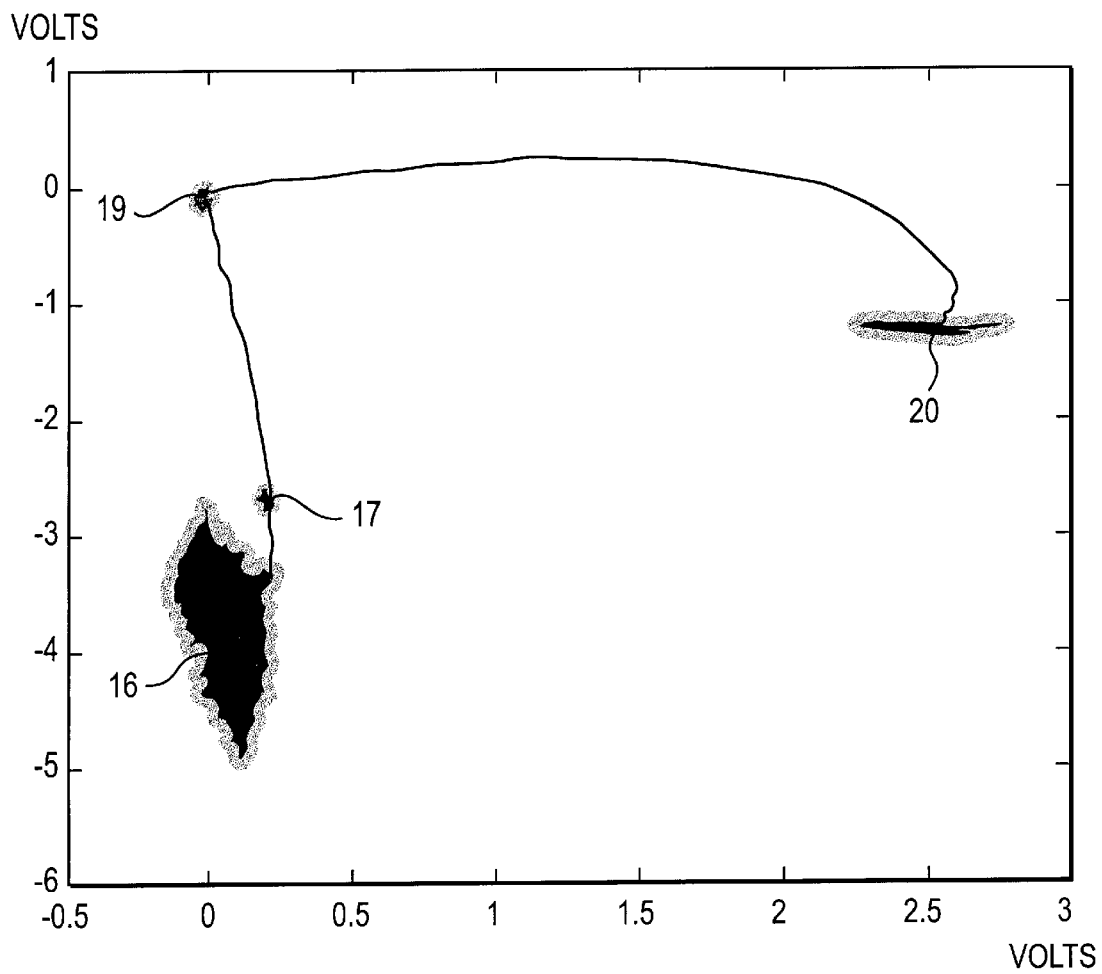
FIG. 5 is an impedance response curve provided by one of the sensors of the specific module.

The impedance representation of the other sensor 14 is not illustrated, but it is identical to that in FIG. 5 apart from a shift in time corresponding to the gap E separating the two sensors 13 and 14. The sensors 13 and 14 each consist, for example, of a coil wound on a ferrite core or of a short coaxial coil.

Figure 6A:
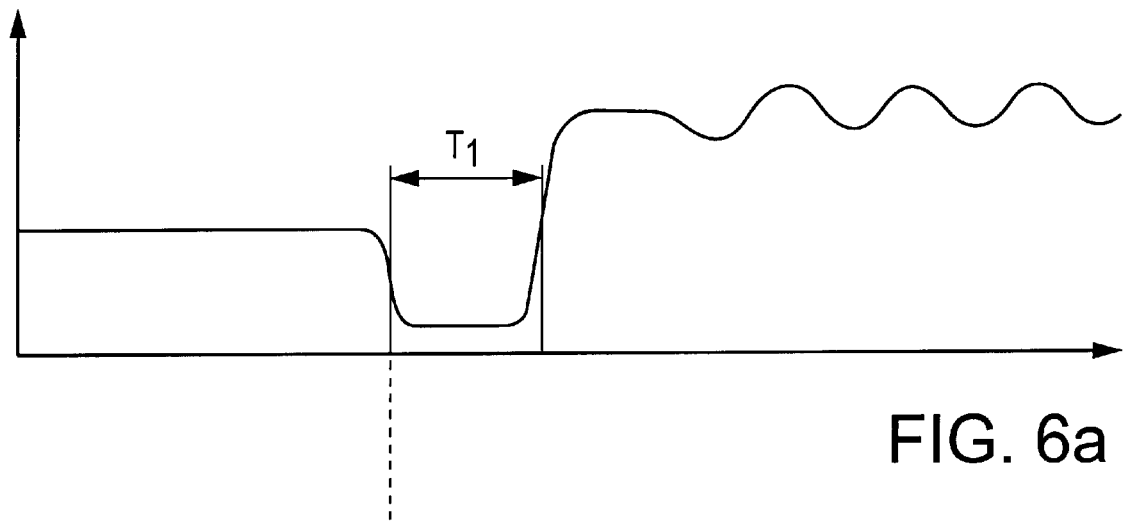
FIGS. 6a and 6b are curves, after processing, of the impedance responses of the two sensors.
Figure 6B:
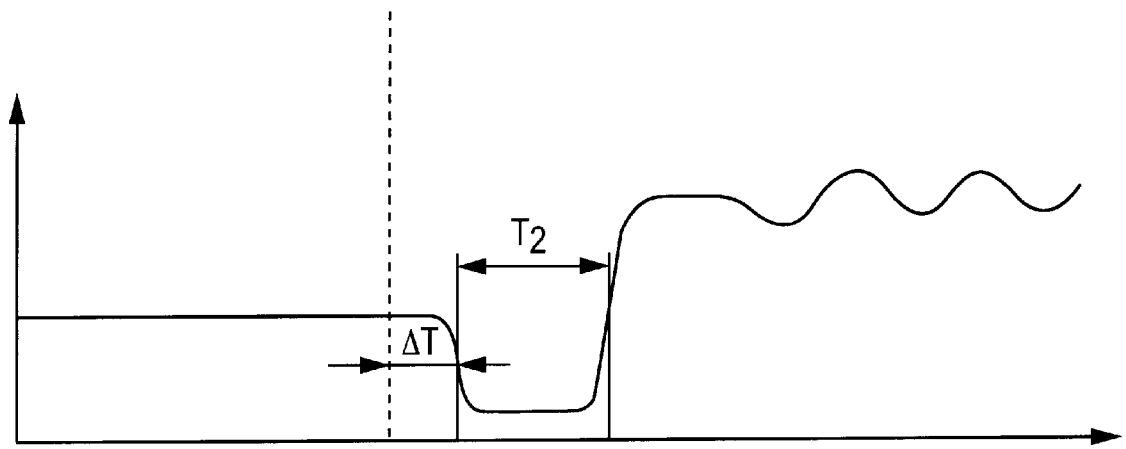

The processing of the variation at the transitions to be detected of the complex impedance of the curve or curves similar to that in FIG. 5 may be carried out by any suitable means, such as Fourier transform spectral analysis or inversion of a mathematical model based on Maxwell's equations, the purpose being to obtain, for each impedance curve, a response of the type illustrated in FIGS. 6a and 6b. In the response shown in FIG. 6a, which corresponds to the sensor 13, it is possible to measure the time $T_1$ taken by the sensor 13 to cross the gap D. Since the timeshift $\Delta T$ between the two sensors for detecting the first transition encountered (the shoulder 10) and the constant gap E which separates the two sensors are known, it is possible to determine the speed $V=E/\Delta T$. Moreover, the gap D is given by the formula $D=V\times T_1$, $=V\times T_2$, since the speed of movement V is regarded as being constant over the interval 18.

In another embodiment, three, or preferably four, sensors are used, two of which 13 and 14 are mounted in tandem on the same generatrix, called the principal generatrix, as illustrated in FIG. 3, the other two sensors 22, 23 being arranged on generatrices lying at 120° to each other and with respect to the principal generatrix. The responses of the sensors make it possible to accurately determine the variation in the initial gap D along several generatrices of the said pipe when the gap D varies from one generatrix to another, especially when the displacement of the inner sheath of the pipe is not uniform over the entire circumference.

The arrangement of the four sensors 13, 14, 22 and 23 is illustrated in the cross section of the pig located to the top and to the right in FIG. 3.

The pig 12, which is known per se, is illustrated in FIG. 3, but it also comprises, according to the invention, a trigger 24 which is mounted at the head. The purpose of the trigger 24, which may consist of an eddy-current sensor for example, is to detect the entrance of the end fitting, so as to trigger the storing of the signals generated by the measurement sensors in at least one memory 25, and preferably in a bank of memories in order to be able to store a large amount of data. The processing of the stored data is carried out after having brought the pig 12 back up to the surface. The pig is of the reversible type and his, at the rear, another head 26 similar to the front head 27. It is during the processing that the impedance curves in FIG. 5 and the response curves in FIGS. 6a and 6b are constructed, the measurement of the gap D or of other distances to be measured being carried out as indicated above.

In another embodiment (not illustrated), it is possible to use, instead of a pig, an umbilical or any other equivalent member which serves to support the sensors and which is inserted into the flexible pipe and which has, at the front end, a trigger for detecting the entrance of the end fitting or each of the end fittings with which the flexible pipe is equipped. As soon as the eddy-current sensors are initialized, they generate signals which are transmitted to the surface, outside the flexible pipe, by means of suitable cables or conductors.

The signals generated by the eddy-current sensors are recorded and stored in one or more memories for the purpose of subsequent or real-time processing. Such a solution makes it possible, by virtue of the trigger which triggers the storing of the signals, to avoid having to move a large memory through the flexible pipe, this memory being the larger the higher the number of gaps to be measured. This is because, by splitting up the memory or memories of the eddy-current sensors, it becomes possible to process and/or measure a large number of gaps without being limited by the memories for storing the data or signals generated by the eddy-current sensors since, whatever the situation, the said storage memories are external to the flexible pipe and are no longer carried by the pig, the excitation of the memories being triggered by the trigger.

It should be noted that the present invention makes it possible to reduce the perturbating influence of the variations in the magnetic permeability $\mu$ and in the electrical conductivity $\sigma$ of the materials used, while still being sensitive to the geometrical variations of the defect or defects to be detected on the internal surface of the flexible pipe and not in the thickness of the materials of which the pipe is composed.

When the speed of movement of the sensors 13 and 14 varies within the interval 18, it is possible to determine the instantaneous speed at each passage over a transition 10 or 11. From the two measured instantaneous speeds at the passage of each transition, it is possible to determine the acceleration within the interval, the said acceleration then being regarded as constant within the interval 18.

What is claimed is:

1. Method for measuring a gap separating a vault of at least one end fitting and a given element of one end of a terminal part of a pipe, the method comprising the steps of:

moving at least two measuring devices along the inside of the pipe, each said device comprising a respective high resolution eddy-current sensor, said at least two sensors being mounted on a common support, said support being movable inside and along the pipe, the sensors being spaced from one another on said support by a fixed distance E;

carrying out at least one series of measurements during the movement of the measuring devices in the end fitting, the measurements comprising the steps of:

detecting in real time with each of said sensors the passage of a pair of consecutive spatial transitions defined respectively by the vault of the end fitting and the end of the terminal part of the pipe;

triggering the measurements for a predetermined time between the detections of said transitions;

storing the measurements in the form of signals in at least one memory; and processing the stored signals in order to determine a time offset $\Delta T$ between detection of a given transition by the two sensors and a time $T_1$ or $T_2$ taken by one of said sensors to run a gap D between the two consecutive transitions, and to determine from the values thus obtained and from said fixed distance E, the value of said gap separating said two consecutive transitions.

2. Method according to claim 1, wherein detecting of the passage of the consecutive transitions comprises the step of measuring a variation in complex impedance of the signals within the distance interval delimited between the transitions.

3. Method according to claim 1, wherein the measurements are obtained by a sensor or sensors used in absolute mode and by the step of real-time processing of the signals which are analyzed by Fourier transform spectral analysis so as to identify sudden changes in the spectrum during said passage between the given element and the vault of the end fitting.

* * * * *